United States Patent [19]

Chiapparelli et al.

[11] Patent Number: 4,870,057

[45] Date of Patent: Sep. 26, 1989

[54] USE OF FRUCTOSE-1,6-DIPHOSPHATE IN THE TREATMENT OF ACUTE ALCOHOLIC INTOXICATION AND CHRONIC ETHYLISM, AND RELATED PHARMACEUTICAL COMPOSITIONS

[75] Inventors: Marco Chiapparelli; Ugo Cavicchia, both of Rome, Italy

[73] Assignee: Biomedica Foscama Industria Chimico-Farmaceutica S.p.A., Rome, Italy

[21] Appl. No.: 208,964

[22] Filed: Jun. 20, 1988

[30] Foreign Application Priority Data

Apr. 11, 1988 [IT] Italy .................................. 47834 A/88

[51] Int. Cl.$^4$ ............................................ C07H 11/04
[52] U.S. Cl. ...................................... 514/23; 514/811; 536/117
[58] Field of Search .................... 514/23, 811; 536/117

[56] References Cited

U.S. PATENT DOCUMENTS

| | | | |
|---|---|---|---|
| 3,066,135 | 11/1962 | Baruchello | 536/117 |
| 3,494,916 | 11/1964 | Napper et al. | 536/117 |
| 3,931,402 | 1/1976 | Ghielmetti et al. | 514/23 |
| 4,448,771 | 5/1984 | Cattani et al. | 514/23 |
| 4,703,040 | 10/1987 | Markov | 536/117 |

Primary Examiner—Ronald W. Griffin
Assistant Examiner—Everett White
Attorney, Agent, or Firm—Walter H. Schneider

[57] ABSTRACT

The present invention relates to the therapeutical use of a pharmaceutical composition of fructose 1,6-diphosphate (FDP) (sodium salt) which, intravenously administered, treats somatic and psychic manifestations caused by alcoholic intoxication.

8 Claims, 2 Drawing Sheets

USE OF FRUCTOSE-1,6-DIPHOSPHATE IN THE TREATMENT OF ACUTE ALCOHOLIC INTOXICATION AND CHRONIC ETHYLISM, AND RELATED PHARMACEUTICAL COMPOSITIONS

The present invention relates to the therapeutical treatment of somatic and psychic manifestations due to alcoholic intoxication, by intravenous administration of fructose-1,6-diphosphate, suitably in the form of sodium salt, $C_6H_{12}Na_2O_{12}P_2$.

An increasing interest in alcoholism and in its treatment has been observed during the last years, since strong drink abuse is the cause of a number of psychic, physical and social pathologies. Organ and system damages in hard drinkers and in alcoholic patients are the result of a repeated exposure of cells and tissues to alcohol and to its main metabolite, acetaldehyde, said exposure being a prolonged cell injury caused by lipid peroxidation with cellular hypoxia, mitochondrion damage and reduction in protein synthesis.

Generally, for patients under acute inebriety, the first and only aim is to remove the drunkenness state. In the treatment of these cases, besides active psychosedatives, when a disinhibition-excitation pattern is present, or nervous stimulants, in case of clear depression of nervous functions, substances considered to quickly reduce alcoholemia are used. Among said substances, glucose pyruvate, alanina, vitamin $B_6$ and pyridoxine-pyrrolidone carboxylate salt are used.

The major part of hospitalized chronic alcoholics show malnutrition signs, varying from subclinical nutritional and vitaminic deficiencies to advanced denutrition conditions ("derelict type" patients of Anglo-Saxon literature). In the latter, body weight is reduced and the values of anthropometric and laboratory parameters evidence a marked impairment of nutritional indexes.

In the malnourished alcoholic, dietary and pharmacologic treatments have a predominant role; on the contrary, the approach to the so-called "florid-type patients" is substantially based on alcohol withdrawal, together with psychopharmacologic therapy and psychological-social supports. In these cases, besides the use of specific drugs to control of psychiatric (benzodiazepines) and neurovegetative (beta-blocking drugs) manifestations, which are present during the alcohol withdrawal phase (Withdrawal Syndrome), hydro-electrolytic balance and metabolic recover are aimed by adding insuline in low doses to enteral and parenteral diets.

Now, it has surprisingly been found that fructose-1,6-diphosphate, intravenously administered, leads to extremely interesting therapeutical results in the treatment of acute alcoholic intoxication, manifestations due to acute alcoholic inebriety, and chronic alcoholism.

1. CLINICAL PHARMACOLOGY

Materials and Methods

Male volunteers (ages 19 to 46, 73 kg average weight) in good conditions of health as ascertained by objective test and hematologic and biochemical analyses, participated in the investigation. None of the subjects had used drugs during the week before the study nor in the course of the study.

Each subject was given, in two sittings, with one wash-out week interval between sittings, ethanol (control) and ethanol with added fructose-1,6-diphosphate (FDP) according to an experimental cross-over design. After one night of fasting, each patient received ethanol orally, in the morning, at a rate of 0.5 g/kg body weight, as a 30% analytical grade ethyl alcohol solution in effervescent mineral water. FDP was administered at the rate of 250 mg/kg of fructose-1,6-diphosphate sodium hydrate salt in an intravenous infusion during 20 minutes (2.5 ml/kg).

From the individual data obtained in each sitting and for each subject, the values of the following parameters were calculated: maximum concentration (Cmax), time for attaining maximum concentration (Tmax), mean life of absorption (Ab t½), mean life of elimination (El t½) and area under curve zero to infinity (AUC). The ethanol and acetaldehyde concentrations were measured in the two sittings of study and the values of the pharmacokinetic parameters given above were compared by the Student's t-test for paired data, with the exception of the maximum concentration times of ethanol which were compared by the Wilcoxon test. The level of statistical significances was set at 5%.

RESULTS

Table 1 shows, for each subject, the ethanol concentrations at the seven times during the two sittings of treatment, control and FDP administration. The mean values at 15, 30 and 60 minutes from administration of ethanol are lower after pretreatment with FDP (p 0.05). The percent difference of the concentrations observed after FDP was 70% at 15 min., 64% at 30 min., 31% at 60 min., with respect to control.

In table 2 the mean values of the pharmacokinetic parameters of ethanol are shown. The average of maximum concentrations in the eight volunteers in higher in the control sitting, 14.13 mmol/l (10.4–17.2 mmol/l range), than inn the FDP pretreatment sitting, 10.75 mmol/l (5.2–17.1 mmol/l range); however, the observed difference did not attain statistical significance.

The time for attaining the maximum concentration, as calculated in the presence of FDP, was 120% (p<0.05) longer than that noted for the control sitting.

The absorption half-life of ethanol is 0.23 h in the control sitting and 0.69 h following infusion with FDP; the comparison between these values (p<0.05) shows a 66% difference in the alcohol absorption rate.

There are no significant differences between the AUC of the control sitting (2695 mmol min/l average) and the AUC relating to the FDP sitting (2229 mmol min/l average). A similar result was obtained for the elimination half-life (2.4 h control average, 2.7 h FDP average) which was calculated only for seven subjects because of the experimental points available for subject 2 not being sufficient.

Hematic concentrations of acetaldehyde resulting from ethanol's metabolism were measured in all the subjects and both the individual values and the averages are given in Table 3. There are no statistically significant differences at any of the considered times.

CONCLUSIONS

The data from this study show FDP to affect ethanol's kinetics in different ways. The absorption rate decreases when FDP is administered before alcohol intake, as is shown by the higher values of both the absorption half-life and the time for attaining maximum concentration, and the concentrations of ethanol at the 60 min. time are much lower following pretreatment with FDP.

The area under the curve and the elimination half-life are, however, not affected to any significant extent by administration of the drug. This might be due to the elimination half-life of the FDP being short, less than 15 minutes, which would prevent the pharmacologic effect from being retained beyond the first hour.

Figure 1:
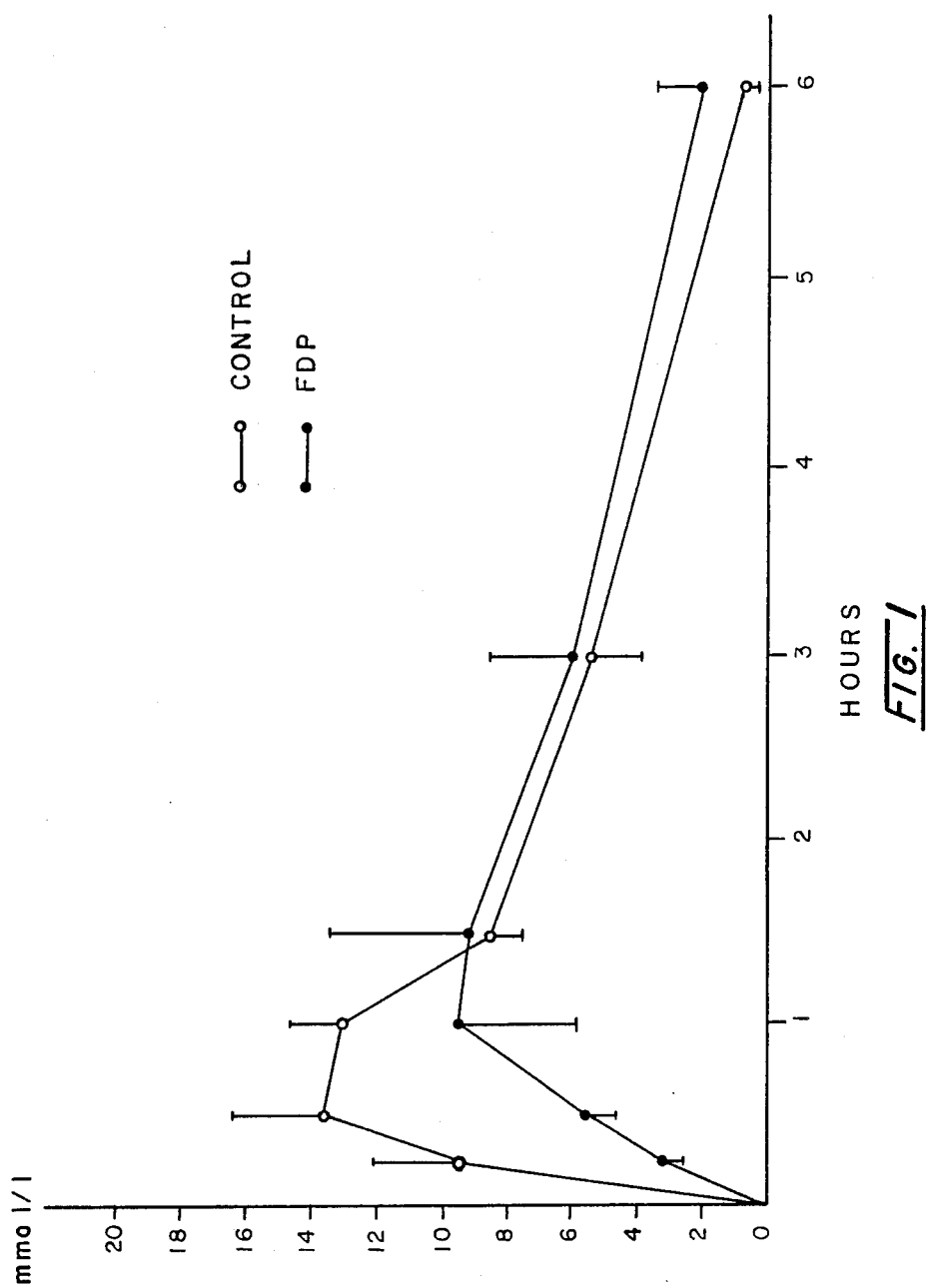
FIG. 1 shows ethanol hematic concentrations (average and SD).
Figure 2:
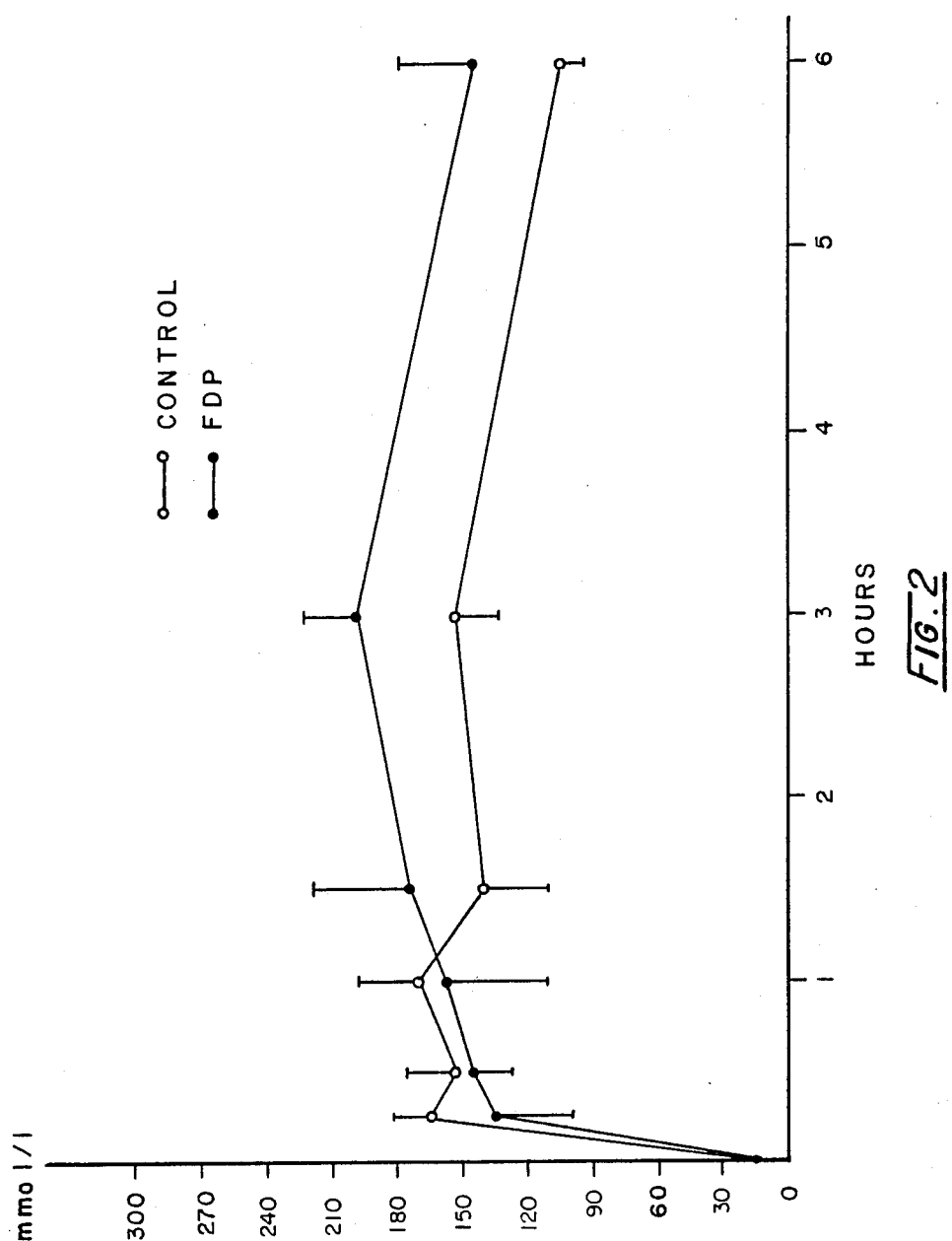
FIG. 2 shows acetaldehyde hematic concentrations (average and SD).

The differences in the times for attaining maximum concentration are consistent in significance with the observed differences in hematic concentrations of ethanol at the 15, 30 and 60 min. times. This would be indicative of an early effect of FDP on the alcohol's metabolism as soon as the drug enters the blood stream. FIG. 1 shows, indeed, that AUC, as calculated in the 0–90 min. range, is 40% lower following administration of FDP.

These data suggest that FDP should be administered in repeated doses at 30 min. intervals in order to affect the elimination rate, after ingestion of alcohol, thereby reducing the total AUC and the maximum concentration, and increasing the curve slope during the disappearance phase.

The data from this preliminary study show that FDP can be helpful in treating acute alcoholic intoxication.

2. ACUTE DRUNKENNESS

Material and Methods 28 patients were selected, 26 males and 2 females, aged 17 to 68, which had been taken to a first aid post for traumas suffered during a state of acute drunkenness (18 cases) or to phenomena resulting from that state of drunkenness (10 cases). Of the patients under observation, 18 were chronic alcoholics and 10 were subjects with no alcoholism story (Table 4). Left out of the study were those subjects who exhibited severe cranial trauma, severe motor derangements or delirium tremens, and drug addicts.

The patients then received, at random, one rapid infusion of 15 g FDP as a 10% sodium salt solution of FDP, or a 5% (150 ml) glucose solution. 15 minutes after the completion of infusion, evaluations were repeated.

Following the first anamnestic and diagnostic checks, measurements were taken of the arterial pressure and the heart rate. Then, evaluation was made, in basal conditions, of the psychic and behavioral state (psychomotor excitement, vigilance, time-space orientation and lucidity) and the neurological state (equilibrium, forefinger-nose test, palpebral, corneal and pain reflexes). For the semiquantitative evaluation of the selected parameters, severity scales with arbitrary ratings were adopted. Evaluation of lucidity was made by using the figure repeating test.

The data obtained for each patient were compared with those obtained before the treatment by means of the mixed pattern variance analysis followed, in case of gross significance, by the Tukey's multiple comparison test. A 5% level was used as the minimum level of statistical significance.

RESULTS

The cardiovascular parameters show (Table 5) that only in those patients who were treated with FDP do the heart rate and the diastolic artieral pressure vary to a significant extent, with the values going from 103 to 94 pulsations/minute and from 68 to 75 mm Hg respectively. Particularly, in subjects who in basal conditions exhibited hypertension accompanied by tachycardia, the effect of FDP is especially manifest and helpful, since it permits the normal values of both blood pressure and heart rate to be restored.

The psychic and behavioral state of the patients (Table 6) evidences a marked improvement as a result of FDP administration. In fact, whereas the slight improvements recorded with glucose solution in no case are statistically significant, with the administration of FDP all of the parameters show to be positively and significantly influenced. More specifically, the state of psychomotor disorder tends towards complete disappearance, while vigilance, orientation and mental lucidity are notably improved, with the tendency being towards return to normal levels. Comparison of the treatments shows that there is a significant difference between FDP and glucose solution in the final values for vigilance and orientation.

As far as the neurological aspect is concerned (Table 7), with glucose solution only mediocre variations are observed, a significance level being solely attained in the case of palpebral reflex. On the contrary, by treatment with FDP, both the postural equilibrium and the forefinger-nose test, as well as the palpebral and pain reflexes are significantly improved. All the patients who, in basal condition, exhibited impairment of the corneal reflex, were normal state in this respect at the end of FDP treatment.

CONCLUSIONS

This study evidences that administration of FDP produces a rapid recovery of mental and behavioral functions as well as of the nuerological and hemodynamic parameters.

In fact, immediately after FDP infusion, the patients showed to be significantly improved in respect of all of the monitored parameters such as excitement state, vigilance level, time-space orientation, degree of mutual lucidity, neurological tests.

Of particular interest, in clinical terms, is the restoring of normal cardio-circulatory parameters in those patients who exhibited marked hypotension and reflected tachycardia on initial observation.

It clearly appears that use of FDP permits results to be registered which are markedly and significantly more pronounced than those produced by spontaneous recovery from intoxication with the time; in fact, with the glucose solution-treated group, in no case are significant improvements noted except for the palepbral reflex.

Therefore, in view of its effectiveness and good tolerability, FDP can stand as a helpful means for safe use in treating disturbances from acute inebriety.

3. CHRONIC ALCOHOLICS AT A STAGE OF DETOXICATION

Material and Methods

The investigation was conducted in 6 centers; a common protocol was adopted and chronic alcoholics were selected whose general conditions met the following criteria: reduced body weight at least 10% less than usual, at least two laboratory tests evidencing values indicative of systemic impairment caused by alcohol: hematocrit<40%, mean corpuscular volume>97 $\mu$m, serum gamma-glutamyl transpeptidase and transaminase values being at least twice in excess of the standard upper limit, bilirubin>1.5 mg/dl, plasma cholesterol<200 mg/dl, plasma albumins<3 g/dl.

This study left out patients more than 70 years old or patients suffering from severe renal or cardiovascular impairment, diabetes or other pathologies (epilepsy, delirium tremens) which could prevent evaluation of the investigated treatment.

During study, which was conducted single blind, two therapeutic procedures were compared for a period of 8 days allotted as follows: one day (I) for selection and basic determinations at the time of alcohol withdrawal; six days (II–VII) for treatment; one day (VIII) for follow-up. The treatment for the control group was as follows: day I, infusion of 10% glucose solution (1.000 ml) and normal saline (500 ml) with added vitamins and trace elements; days II to VIII, mixed enteral hypercaloric nutrition (about 2.400 cal/die). The FDP treated group received in addition, days II–VII, fructose-1,6-diphosphate, 10 g every 12 hours (20 g/day), as a rapid infusion (5–10 min) of a 10% hydrate sodium salt solution of FDP. Some of the patients received, days II to IV, a total parenteral nutrition (NTP) followed by hypercaloric diet during the remaining three days.

During the study, no further drugs were administered except those which would be required by concomitant pathologies and which could not interfere with the nutritional state. In the patients imperatively requiring a control of psychomotor derangement during the abstinence period, chlordimethyldiazepam (2 mg/iv) was used and the daily doses thereof were recorded.

On the first day the history, particularly in respect of alcoholism, was obtained. On days I, V and VIII a thorough examination of the patient's neurological and psychiatric conditions was performed. The psychic areas were evaluated by using simplified rating scales for the psychomotor derangement and the behaviour and consciousness disorders present in the alcohol withdrawal period. For the neurological evaluation, there were taken into consideration the reflexes, the exteroceptive and propioceptive sensitivities and the presence of ataxia, tremors and cramps, and semiquantitative ratings of 0 (no symptom or normal picture) to 3 (high severity symptom or no response) were assigned.

Hematologic and biochemical tests as required for patient's definition and laboratory evaluation were performed on blood samples obtained both in basal conditions and at the end of treatment.

The data relating to the neurological and psychiatric conditions were analyzed by the statistical Wilcoxon two-sample test and a value of p less than 0.01 was set as the significance level.

RESULTS

A total of 67 patients participated to the study and were divided into two groups (Table 8) which were comparable with regard to both the general clinical characteristics of the patients and their consistency with the grouping criteria.

As for as the adopted type of diet is concerned, 51 patients (26 in the control group, 25 in the FDP treated group) were given the standard oral diet during the entire study, while 16 patients (6 in control group, 10 in FDP group) received a three-day NPT diet followed by oral diet.

Psychiatric symptoms (Table 9):

The most frequent disturbance was represented by the behavior disorders (23 cases in control group, 25 in the FDP treated group) whereas less usual disturbances were the psychomotor dearrangements (17 and 20 cases, respectively) and the consciousness disorders (11 in control group, 10 in FDP group).

Evolutive tendency of the psychiatric disturbances present at the time of alcohol withdrawal shows an improvement in the patients of both the treated groups.

However, an analysis of the severity ratings shows, in general, a faster recovery in FDP treated patients. In fact, on day V, only these latter showed an improvement of all of the considered symptoms ($p<0.01$). On the eighth day, a diminution of the psychomotor derangement and an improvement of the vigilance were observed in both groups; however, the consciousness disorders did disappear in FDP treated patients but did not in the control group.

Neurological symptoms (Table 10):

A reduction in reflexes and sensitivity was present in 20 patients of the control group and 21 of the FDP group, while ataxia, tremors and cramps were observed in 29 patients of the control group and 32 of the FDP group.

As far as the impairment of reflexes is concerned, a significant difference is observed between the two treated groups; in fact, only in the FDP treated group the reflexes recovered to normal (on day VIII). Evolutive tendency of the remaining neurological symptomatology does not evidence any difference between the two treatments, in that the patients in both groups showed a general reduction of the anomalies in the course of the study.

CONCLUSIONS

The chronic alcoholics exhibited a large variety of systemic organic (gastrointestinal, pancreatic, hepatic and hematologic) alterations, with or without nutritional impairment. This study left out florid-type patients and only admitted those patients in compromised conditions of nutrition which would allow evaluating immediate effects of a nutritional metabolic scheme of treatment during the alcohol withdrawal stage.

The nutritional scheme associated with FDP proved to be an effective approach capable of accelerating the clinical recovery of the patients. In fact, the psychiatric symptomatology connected with the alcohol withdrawal in the initial period of cure, disappeared after only five days of treatment in patients treated with FDP.

A further demonstration of the effectiveness of the FDP-associated scheme of treatment in controlling the psychiatric symptomatology, is the higher consumption of chlordimethyldiazepam required by patients not having get FDP.

Protection offered by FDP to impaired alcoholic patients appears to be a fact of clinical interest and it suggests that the drug, when associated with a nutritional support scheme in the initial stages of treatment, can accelerate the recovery of starving chronic alcoholic patients, thereby reducing both observation and hospitalization times.

TABLE 1

Ethanol hematic concentrations (mmol/l)

| Subject | 0 | 15 | 30 | 60 | 90 | 180 | 360 |
|---|---|---|---|---|---|---|---|
| | | | | Time (min) | | | |

CONTROL SESSION

| Subject | 0 | 15 | 30 | 60 | 90 | 180 | 360 |
|---|---|---|---|---|---|---|---|
| 1 | <0.07 | 6.3 | 9.4 | 11.7 | 7.0 | 3.7 | 1.0 |
| 2 | <0.07 | 13.4 | 17.2 | 15.6 | 9.4 | 8.3 | 0.8 |
| 3 | <0.07 | 7.4 | 10.4 | [9.8] | 9.2 | 5.7 | 0.8 |
| 4 | <0.07 | 12.2 | 16.5 | 13.3 | 8.6 | 6.1 | 0.8 |
| 5 | <0.07 | 8.6 | 15.4 | 13.2 | 8.5 | 6.1 | 0.8 |
| 6 | <0.07 | [6.7] | 12.4 | 14.1 | 9.1 | 4.2 | 0.8 |
| 7 | <0.07 | 8.1 | 13.2 | 10.9 | 7.5 | [4.2] | 0.9 |
| 8 | <0.07 | 10.2 | 14.6 | 13.1 | 8.4 | 4.3 | 0.9 |
| Average | — | 9.48 | 13.65 | 12.71 | 8.46 | 5.49 | 0.85 |
| (SD) | — | (2.59) | (2.81) | (1.70) | (0.79) | (1.59) | (0.07) |

FDP SESSION

| Subject | 0 | 15 | 30 | 60 | 90 | 180 | 360 |
|---|---|---|---|---|---|---|---|
| 1 | <0.07 | 3.9 | 5.8 | 10.6 | 5.3 | 2.7 | 1.0 |
| 2 | <0.07 | 0.5 | 2.0 | 2.2 | 3.9 | 5.2 | 4.0 |
| 3 | <0.07 | 2.1 | 4.9 | 10.9 | 17.1 | 10.2 | 1.3 |
| 4 | <0.07 | 3.6 | 6.4 | 14.8 | 10.4 | 5.1 | 0.2 |
| 5 | <0.07 | 2.9 | 4.4 | 9.6 | 11.6 | [7.4] | 3.2 |
| 6 | <0.07 | 3.5 | 5.6 | 8.4 | 10.4 | 7.4 | 3.7 |
| 7 | <0.07 | 3.7 | 6.1 | [5.9] | 5.7 | 3.6 | 1.2 |
| 8 | <0.07 | 2.9 | 4.7 | 10.2 | 9.2 | 7.4 | 2.6 |
| Average | — | 2.88 | 4.98 | 9.08 | 9.20 | 5.94 | 2.15 |
| (SD) | — | (1.14) | (1.39) | (3.49) | (3.97) | (2.59) | (1.41) |
| | | ** | ** | * | | | |

(n) Calculated value (missing) Student's t test for coupled data
*p < .05 vs control
**p < .01 vs control

TABLE 2

Ethanol pharmacokinetic parameters: average values (DS)

| Parameter (unit) | n | CONTROL | SESSION | FDP | SESSION | | |
|---|---|---|---|---|---|---|---|
| Cmax (mmol/l) | 8 | 14.13 | (2.17) | 10.75 | (3.71) | | (1) |
| Tmax (min) | 8 | 37.50 | (12.90) | 82.56 | (41.75) | * | (2) |
| Ab t½ (h) | 8 | 0.23 | (.13) | 0.69 | (.37) | * | (1) |
| El t½ (h) | 7 | 2.40 | (.30) | 2.70 | (.90) | | (1) |
| AUC (mmol.min/l) | 8 | 2229 | (345) | 2695 | (976) | | (1) |

* = p < .05 vs Control
(1) Student's t test for coupled data
(2) Wilcoxon test

TABLE 3

Acetaldehyde hematic concentrations (micromol/l)

| Subject | 0 | 15 | 30 | 60 | 90 | 180 | 360 |
|---|---|---|---|---|---|---|---|
| | | | | TIME (min) | | | |

CONTROL SESSION

| Subject | 0 | 15 | 30 | 60 | 90 | 180 | 360 |
|---|---|---|---|---|---|---|---|
| 1 | <20 | 143 | 157 | 196 | 95 | 131 | 96 |
| 2 | <20 | 184 | 179 | 198 | 145 | 181 | 124 |
| 3 | <20 | 174 | 117 | 130 | 114 | 145 | 101 |
| 4 | <20 | 149 | 171 | 151 | 127 | 135 | 97 |
| 5 | <20 | 164 | 158 | 183 | 161 | 176 | 110 |
| 6 | <20 | 158 | 123 | 191 | 155 | 150 | 120 |
| 7 | <20 | 181 | 171 | 183 | 173 | 140 | 116 |
| 8 | <20 | 174 | 144 | 140 | 125 | 171 | 99 |
| Average | — | 165.8 | 152.7 | 171.6 | 140.9 | 153.8 | 107.9 |
| (SD) | — | (15.1) | (22.8) | (27.0) | (29.4) | (19.8) | (10.9) |

FDP SESSION

| Subject | 0 | 15 | 30 | 60 | 90 | 180 | 360 |
|---|---|---|---|---|---|---|---|
| 1 | <20 | 103 | 130 | 128 | 146 | 108 | 111 |
| 2 | <20 | 73 | 139 | 109 | 123 | 177 | 167 |
| 3 | <20 | 171 | 199 | 230 | 242 | 244 | 186 |
| 4 | <20 | 114 | 153 | 174 | 148 | 185 | 134 |
| 5 | <20 | 168 | 164 | 204 | 200 | 190 | 169 |
| 6 | <20 | 165 | 147 | 188 | 153 | 188 | 101 |
| 7 | <20 | 131 | 150 | 106 | 226 | 213 | 189 |
| 8 | <20 | 151 | 135 | 125 | 163 | 191 | 105 |
| Average | — | 134.5 | 152.3 | 158.1 | 175.4 | 187.1 | 145.5 |
| (SD) | — | (35.6) | (21.8) | (47.1) | (42.5) | (38.5) | (36.8) |

FDP vs Control: ns
Student's t test for coupled data

TABLE 4

General characteristics of the patients

| PARAMETER | GLUCOSATE SOLUTION | | FDP | |
|---|---|---|---|---|
| MALE/FEMALE | 12 | 1 | 14 | 1 |
| AGE (years) | | | | |
| Mean | 40.5 | | 36.7 | |
| Range | 18–68 | | 17–59 | |
| KIND OF ETHYLISM | | | | |
| Chronic ethylism | 8 | | 10 | |
| Occasional ethylism | 5 | | 5 | |

TABLE 5

Vital signals in the two treatment groups

| PARAMETER | GLUCOSATE SOLUTION | | FDP | |
|---|---|---|---|---|
| | Basal | Final | Basal | Final |
| CARDIAC FREQUENCY (beats/minute) | 101.7 | 96.9 | 103.1 | 94.4** |
| ARTERIAL DIASTOLIC PRESSURE (mm Hg) | 69.6 | 69.6 | 67.9 | 75.3* |
| ARTERIAL SISTOLIC PRESSURE (mm Hg) | 113.1 | 110.8 | 113.2 | 116.5 |

*p < 0.05 vs Basal
Tukey's test
**p < 0.01 vs Basal

TABLE 6

Scores concerning psychic and behavioural conditions

| PARAMETERS | GLUCOSATE Basal | GLUCOSATE Final | FDP Basal | FDP Final |
|---|---|---|---|---|
| MOTOR DERANGEMENT | 1.0 | 0.7 | 1.1 | 0.3** |
| VIGILANCE IMPAIRMENT | 1.2 | 1.0* | 1.1 | 0.5** |
| ORIENTATION IMPAIRMENT | 4.3 | 3.4* | 4.5 | 1.7** |
| LUCIDITY LEVEL | 1.5 | 2.5 | 1.6 | 3.6** |

*$p < 0.05$ vs Final FDP
**$p < 0.01$ vs Basal
Tukey's test

TABLE 7

Impairment scores in neurologic tests

| PARAMETER | GLUCOSATE Basal | GLUCOSATE Final | FRD Basal | FRD Final |
|---|---|---|---|---|
| EQUILIBRIUM | 1.1 | 0.9 | 1.6 | 1.1** |
| "FOREFINGER-NOSE" TEST | 0.9 | 0.7 | 1.3 | 0.4** |
| PALPEBRAL REFLEX | 0.5 | 0.1* | 0.4 | 0.0* |
| CORNEAL REFLEX | 0.1 | 0.1 | 0.1 | 0.0 |
| PAIN REFLEX | 0.5 | 0.2 | 0.9 | 0.3* |

*$p < 0.05$ vs Basal
**$p < 0.01$ vs Basal
Tukey's test

TABLE 8

General characteristics of the patients

| PARAMETER | CONTROL GROUP | FDP GROUP |
|---|---|---|
| MALES/FEMALES | 27  5 | 28  7 |
| AGE (years) | | |
| Mean | 48.2 | 47.8 |
| Median | 48 | 49 |
| Range | 27–61 | 30–60 |
| WEIGHT (kg) | | |
| Mean | 58.7 | 58.6 |
| Range | 41–78 | 40–79 |
| REDUCTION IN WEIGHT (%) | | |
| Mean | 15 | 13 |
| Range | 8–43 | 5–33 |

TABLE 9

Scores concerning psychic and behavioural state

| PARAMETER | CONTROL B | CONTROL V | CONTROL VIII | FDP B | FDP V | FDP VIII |
|---|---|---|---|---|---|---|
| MOTOR DERANGEMENT | 1.3 | 0.8 | 0.5** | 1.4 | 0.6** | 0.4** |
| BEHAVIOURAL DISORDERS | 1.2 | 0.7 | 0.5** | 1.3 | 0.4** | 0.3** |
| CONSCIENCE DISORDERS | 1.0 | 0.6 | 0.5 | 1.5 | 0.3** | 0.2** |

**$p < 0.01$ vs Basal
Wilcoxon test

TABLE 10

Impairment scores in neurological tests

| PARAMETER | CONTROL B | CONTROL V | CONTROL VIII | FDP B | FDP V | FDP VIII |
|---|---|---|---|---|---|---|
| REFLEXES | 1.4 | 1.2 | 1.2 | 1.6 | 1.2 | 1.0** |
| SENSITIVITY | 3.3 | 2.4** | 1.7** | 3.0 | 2.1** | 1.8** |
| ATAXIA-TREMORS CRAMPS | 1.5 | 0.9** | 0.8** | 1.7 | 1.0** | 0.5** |

**$p < 0.01$ vs Basal
Wilcoxon test

The present invention relates to all the industrially applicable aspects connected with the use of fructose-1,6-diphosphate, suitably in form of sodium salt, as a principle able to correct the somatic and/or psychic manifestations caused by alcoholic intoxication. An essential aspect of the invention is therefore represented by pharmaceutical compositions containing, as the active principle, therapeutically effective amounts of fructose-1,6-diphosphate, in particular in form of sodium salt, as well as optional excipients conventionally used in the pharmaceutical techniques; and by pharmaceutical compositions containing moreover other active priciples suitable for the therapy of manifestations of alcoholic intoxication, as long as they ae compatible with fructose-1,6-diphosphate.

Daily doses to be administered range from 100 to 400 mg/kg of body weight, preferably ranging from 250 mg/kg. Non limiting examples of pharmaceutical formulations are ampuls for phleboclysis containing 10-20-50 g of fructose-1,6-diphosphate sodium salt ($C_6H_{12}Na_2O_{12}P_2$), in microcrystalline or lyophilized form, to be diluted with 100-200-500 ml of apyrogenetic bidistilled water.

We claim:

1. A method of treating a patient suffering from acute alcohol intoxication to reduce blood alcohol level and improve impaired vital signs, sensorimotor functions and psychic pattern and behavior symptoms which comprises intraveneously administering to said patient while intoxicated a therapeutically effective amount of fructose-1,6-diphosphate.

2. A method according to claim 1 in which the fructose-1,6-diphosphate is intraveneously administered in the form of its sodium salt.

3. A method according to claim 2 in which the therapeutically effective amount of fructose-1,6-diphosphate is 100–400 mg/kg of patient body weight per day.

4. A method according to claim 3 in which said fructose-1,6-diphosphate is intraveneously administered as a single dose of 15 grams.

5. A method of treating a patient suffering from chronic alcohol intoxication to accelerate recovery and improve sensorimotor functions and psychic pattern and behavior symptoms which comprises intraveneously administering to said patient while in a state of alcohol abstinence a therapeutically effective amount of fructose-1,6-diphosphate.

6. A method according to claim 5 in which the fructose-1,6-diphosphate is intraveneously administered in the form of its sodium salt.

7. A method according to claim 6 in which the therapeutically effective amount of fructose-1,6-diphosphate is 100–400 mg/kg of patient body weight per day.

8. A method according to claim 7 in which said fructose-1,6-diphosphate is administered in single doses of 10 grams each every 12 hours over a period of six days.

* * * * *